United States Patent
Azuma et al.

(10) Patent No.: US 6,511,428 B1
(45) Date of Patent: Jan. 28, 2003

(54) ULTRASONIC MEDICAL TREATING DEVICE

(75) Inventors: Takashi Azuma, Kodaira (JP); Kenichi Kawabata, Kodaira (JP); Shinichiro Umemura, Hachioji (JP); Kazuaki Sasaki, Kokubunji (JP); Katsuhiro Kuroda, Hachioji (JP); Ryuichi Shinomura, Higashimatsuyama (JP); Yuichi Miwa, Chofu (JP); Kazunari Ishida, Kashiwa (JP); Jun Kubota, Nagareyama (JP)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/830,423
(22) PCT Filed: Oct. 22, 1999
(86) PCT No.: PCT/JP99/05827
§ 371 (c)(1), (2), (4) Date: Apr. 26, 2001
(87) PCT Pub. No.: WO00/24328
PCT Pub. Date: May 4, 2000

(30) Foreign Application Priority Data

Oct. 26, 1998 (JP) .......................................... 10-303616

(51) Int. Cl.[7] .................................................. A61B 8/00
(52) U.S. Cl. .......................... 600/439; 604/22; 606/27; 601/2; 601/3
(58) Field of Search .......................... 600/439; 604/22; 606/27; 601/2–3

(56) References Cited

U.S. PATENT DOCUMENTS

| | | | | |
|---|---|---|---|---|
| 5,036,855 A | * | 8/1991 | Fry et al. ................ | 128/660.03 |
| 5,470,350 A | * | 11/1995 | Buchholtz et al. ............ | 607/97 |
| 5,474,071 A | | 12/1995 | Chapelon et al. | |
| 5,523,058 A | | 6/1996 | Umemura et al. | |
| 5,526,815 A | * | 6/1996 | Granz et al. ........... | 128/660.03 |
| 5,624,382 A | * | 4/1997 | Oppelt et al. ................... | 601/2 |
| 5,676,692 A | | 10/1997 | Sanghvi et al. | |
| 5,720,287 A | * | 2/1998 | Chapelon et al. ...... | 128/660.03 |
| 5,817,021 A | | 10/1998 | Reichenberger | |
| 6,106,517 A | * | 8/2000 | Zupkas ........................ | 606/20 |

* cited by examiner

Primary Examiner—Teresa Walberg
Assistant Examiner—Shawntina T. Fuqua
(74) Attorney, Agent, or Firm—Mattingly, Stanger & Malur, P.C.

(57) ABSTRACT

An ultrasound therapy apparatus delivers focused ultrasound for therapeutical purposes which can be correctly targeted to a target region, and also, a positional shift from the target region under irradiation of ultrasound can be effectively avoided. An ultrasound transducer is inside an applicator with an imaging ultrasonic probe. Another ultrasound transducer monitors a position of a target and a positional shift is inside a catheter which is inserted into a urethral tube. An imaging system drives the ultrasound probe to display an ultrasound tomographic image of a region in the vicinity of a target region. The ultrasound transducer is driven in a pulse-shaped mode at the same frequency as the imaging ultrasound and also at such timing when the imaging ultrasound is reached. As a result, a point-shaped sound source image is superimposed and displayed on an ultrasound tomographic image.

9 Claims, 6 Drawing Sheets

ULTRASONIC MEDICAL TREATING DEVICE

TECHNICAL FIELD

The present invention is related to an ultrasound therapy system for irradiating focused ultrasound used in medical treatments, and more specifically, is directed to such an ultrasound therapy system equipped with an intraluminal catheter functioning as a supplementary role of medical treatments.

BACKGROUND ART

Various therapeutical methods are known in the field so s to execute minimally invasive tissue treatments by irradiating ultrasound from an outside of a body, or in an intraluminal manner. For instance, there is such a therapeutical method for a prostate by employing an ultrasound generator which is arranged inside a rectum.

As an example of ultrasonic therapy applicable to a disease related to a prostate, a prostatomegaly may be cited. A prostatomegaly implies such a disease that since at least a portion of a prostate becomes a hypertrophy, a urethra is bent, so that a patient must conspicuously have an obstruction of a urinary stream, an urgency of voiding, and a frequent urination. As therapeutical methods, the following methods have been proposed, namely, a method for removing a disease portion by a surgical operation, and a method for burning out a disease portion by irradiating a laser thereto. In contrast with these methods, when the ultrasound therapy apparatus disclosed in U.S. Pat. No. 5,676,692 is employed, medical operations can be carried out in a simpler manner, and also an early recovery from the medical operation could be expected. This ultrasound therapy apparatus is arranged by the therapeutical probe, the ultrasonic diagnostic apparatus connected to the therapeutical probe, the power supply used to generate the focused ultrasound, and also the urethral catheter for reflecting the ultrasound. This therapeutical probe contains the focused ultrasound generating source having the two roles, namely, the generation of the continuous wave for therapeutical purposes, and also the generation of the pulse wave used to acquire the ultrasound tomographic image. As the therapeutical method, under such a condition that the catheter is firstly inserted from a urethra to a bladder, the ultrasonic tomographic apparatus probe is inserted into a rectum so as to acquire an ultrasonic tomographic image of a region in the vicinity of the urethra. Thus, a target region for medical treatment is previously determined. Next, the therapeutical probe is inserted into the rectum, and the ultrasonic tomographic image of the region in the vicinity of the prostate is acquired from the ultrasonic pulse signal derived from the therapeutical probe. In this ultrasound therapy apparatus, the ultrasound-generating source for ultrasonic tomographic images may have another function of the therapeutical ultrasound generating source capable of irradiating the continuous wave, it is practically difficult to optimize this ultrasound generating source in order to generate such a pulse wave used to produce the diagnostic tomographic image. That is, it is practically difficult to obtain tomographic images having better image qualities. As a consequence, in this therapy apparatus, while the catheter having the function capable of reflecting the ultrasound is employed, this apparatus is arranged in such a manner that the reflection signals having the strong strengths can be obtained from the catheter. Since the position of the catheter within the tomographic image is confirmed, such a confirmation is made of the position of the target region for treatment within the tomographic image obtained by employing this therapy apparatus. This treatment target region is indicated in such a tomographic image which has been previously acquired by using the ultrasonic tomographic apparatus probe. After the above-described operations have been carried out, the ultrasound for therapeutical purposes is irradiated from the therapeutical probe to the treatment target region. Normally, a time duration required for irradiating ultrasound one time is approximated to several seconds. In the case that a plurality of target regions are medically treated, normally, intervals of approximately 15 seconds are induced. The therapeutical effects may be conceived by the following reason. That is, since the ultrasound is irradiated onto a tissue, this tissue is heated at such a temperature higher than, or equal to the temperature at which this tissue is brought into the thermo-coagulation.

On the other hand, in the case that ultrasound is irradiated onto a living body, it is known that such a cavitation phenomenon may occur other than the heating effect. In this cavitation phenomenon, bubbles called as "cavitation" are produced and will collasp after being grown. Since both the chemical effect and the mechanical effect can be obtained by this cavitation phenomenon, also in the therapeutical operation using the ultrasound, therapeutical effects may be achieved by actively producing the cavitation and by solely utilizing the chemical effect and/or the mechanical effect achieved by this cavitation, or by combining these chemical/mechanical effects with the heating effect by the ultrasound. In such a case that ultrasound is irradiated from an inrectum portion toward a prostate and the like, this ultrasound may constitute a progressive wave condition. However, usually, cavitation can be hardly produced under such a progressive wave condition. To easily produce such a cavitation, the following fact is known. That is, while a substance and the like, which may reflect ultrasound, are employed, the ultrasound is advantageously irradiated under a standing wave condition. In the therapeutical method described in the above-explained U.S. Pat. No. 5,676,692, the reason why the catheter having the feature of reflecting the ultrasound is employed is intended to this cavitation effect. In other words, on the side of the ultrasound generating source for therapeutical purposes from the catheter, the ultrasound directly reached from the ultrasound generating source for therapeutical purposes is overlapped with the reflection wave from the catheter, so that the temperature increase can be effectively achieved. In addition thereto, since the progressive wave produced from the ultrasound generating source for therapeutical purposes and the reflection wave from the catheter may produce the standing wave, the cavitation effect can be promoted.

As previously disclosed in U.S. Pat. No. 5,523,058, with respect to this cavitation technique, the following fact is known. That is, since one frequency component is superimposed on a doubled frequency component, such ultrasound having a waveform suitable for this cavitation may be obtained even under the progressive wave condition.

DISCLOSURE OF INVENTION

Roughly speaking, there are three problems in the conventional therapeutical methods for the prostatomegaly with employment of the focused ultrasound.

As a first problem, the conditions of the prostate cannot be confirmed during medical treatments. In the case that the prostate is brought into the prostatomegaly state, even if the prostatomegaly portion is cut out, since this cut prostate will normally recur after a predetermined time period has passed, such a medical treatment must be carried out many times. To extend a treatment interval, it is desirable to remove such a prostatomegaly portion having a permittably wide area within a single medical treatment. On the other hand, in order to improve a quality of life after medical operation, it is desirable to avoid such irradiation of ultrasound onto a sphincter:muscle and an outlet of seminal vesicle. In the conventional therapy apparatus, since the energy of the focused ultrasound for therapeutic purposes is considerably larger than the energy of the ultrasound used to acquire the diagnostic image, the tissue tomographic image could not be acquired while the therapeutical ultrasound is irradiated, because of the reflection waves and the scattering waves caused by the therapeutical ultrasound. As a result, while the conventional therapy apparatus is employed, the suddenly-occurring positional shifts during herapeutical ultrasound irradiation cannot be properly corrected. In such a case that the medical treatment capable of achieving the high quality of life after the medical operation is wanted to be realized, the ultrasound could be irradiated only to such a narrow region, while excluding not only the region to which the ultrasound should be avoidably irradiated, but also an area located within a predetermined range (for example, 2 cm) from this irradiation avoidable region. As previously explained, in the conventional therapy apparatus, since the conditions of the prostate cannot be confirmed during the medical treatment, the following problem arises. That is, it is practically difficult to realize at the same time both achieving of the quality of life, and excising of the prostate over the wide range.

As a second problem, the energy owned by the focused ultrasound could not be concentrated to the treatment region in a high efficiency. In the conventional technique, the standing wave is produced based upon the reflection waves reflected from the urethral catheter. However, since the reflection waves are used, the amplitudes and the radiation directions of these reflection waves could not be controlled. Therefore, it is expected to promote the cavitation, which is not caused by the reflection waves from the catheter.

As a third problem, both the treatment region and the treatment range can be hardly controlled.

In general, a strength of ultrasound used in a medical treatment is wanted to be such a large value by which a temperature of a tissue can be increased higher than, or equal to a thermocoagulation temperature of this tissue for several seconds. Strengths of ultrasound which are sufficiently required so as to coagulate protein will differ from each other, depending upon conditions. In the conventional therapy apparatus, since it is normally difficult to confirm the coagulation of the tissue by checking a change contained in the ultrasound image, such ultrasound having sufficiently large strengths must be used. However, as explained above, if the medical treatment is carried out while the strength of the ultrasound is fixed to such a value which has been determined before the medical operation, then the strengths of the ultrasound may become excessively large, depending upon a certain condition. As a result, boiling happens to occur near a focal point of the ultrasound, and therefore, bubbles may be produced. When such bubbles are produced, energy of the ultrasound is reflected toward the transducer that generated the focused ultrasound. As a consequence, such a region whose ultrasound intensity is high will occur in front of this focal point. A boiling phenomenon may occur in such a region whose ultrasound intensity is high, and which is located in front of the focal point, and thus, bubbles are produced. Furthermore, another region whose ultrasound intensity becomes high may occur in front of the focal point. As a consequence, if the boiling phenomenon occurs in the vicinity of the focal point, then such a region whose ultrasound intensity is high may successively appear in front of the focal point. When this phenomenon occurs, the coagulation caused by the ultrasound may occur in an avalanche manner, so that the coagulated region is gradually extended toward the transducer that generated the focused ultrasound. In the worst case, the regions up to the rectum wall would be thermally denatured. The conventional therapy apparatus could not properly avoid such an avalanche extension of the coagulated region which is caused by productions of such bubbles.

As a consequence, an object of the present invention is to provide such an ultrasound therapy apparatus (system) capable of confirming an irradiation region of focused ultrasound in high precision, and thus capable of readily increasing an efficiency of a medical treatment.

Another object of the present invention is to provide an ultrasound therapy apparatus (system) capable of readily controlling a generation of cavitation.

A further object of the present invention is to provide an ultrasound therapy apparatus (system) capable of previously avoiding such an event that unnecessary and harmful thermo-denaturation would be conducted into any region other than a target region, which is caused by excessively irradiating ultrasound, and by extending a boiling area due to generations of bubbles.

An ultrasound therapy apparatus, according to an aspect of the present invention, is featured by such an ultrasound therapy apparatus comprising: a first ultrasound transducer for generating focused ultrasound used in therapeutical purposes; an ultrasound probe arranged in such a manner that the ultrasound probe is moved in combination with the first ultrasound transducer; an intraluminal catheter used to be inserted into a region in the vicinity of an irradiation target region of the focused ultrasound; and imaging means for forming an ultrasound tomographic image in such a manner that while imaging ultrasound is repeatedly transmitted from the ultrasound probe, reflection wave responses are acquired by sequentially scanning reception signals of reflection signals thereof along a lateral direction; wherein: the intraluminal catheter is comprised of: a second ultrasound transducer; and drive means for driving the second ultrasound transducer to generate ultrasound during an imaging operation by the ultrasound imaging means; and also the imaging means superimposes a sound source image which is caused by the ultrasound produced by the second ultrasound transducer on the ultrasound tomographic image.

Even while the focused ultrasound is irradiated, the above-explained sound source image clearly indicates the position of the second ultrasound transducer (position of imaging means, namely relative position of this imaging means with respect to focused ultrasound for therapeutical purpose). In the case that after the position of the second ultrasound transducer has been previously set to a region in the vicinity of the target region for ultrasound irradiation by positioning the catheter at a certain depth within the body cavity, the imaging operation is carried out, it is possible to monitor as to whether or not the focused ultrasound is correctly irradiated onto the target region with reference to the above-described sound source image. Even while the focused ultrasound is irradiated, it is possible to monitor as to whether or not the focused ultrasound is correctly irradiated onto the target region.

When the above-described second ultrasound transducer is driven by the continuous wave, the above-described sound source image becomes a line-shaped image, and thus, indicates only azimuth where the second ultrasound transducer is located. In this case, assuming now that the drive means may drive the second ultrasound transducer in a pulse-shaped mode, the ultrasound therapy apparatus is further comprised of a setting means for setting that the drive timing of the second ultrasound transducer is adjustable with respect to the repetitive ultrasound transmission by the imaging means. As a result, the above-explained sound source image becomes such a point-shaped image which may have information as to not only the azimuth direction, but also the depth direction of the ultrasound transducer. Under such a condition that the above-explained setting means is previously adjusted in such a way that the image of the second ultrasound transducer produced by the reflection waves is overlapped with the above-explained sound source image produced by the pulse-wave driving operation while observing the ultrasound tomographic image, and thereafter, both the pulse-wave driving operation of the transducer and the imaging operation of the tomographic image are repeatedly carried out while keeping this setting condition, the above-explained sound source image can continuously indicate the position of the second ultrasound transducer in the correct manner.

Instead of the above-explained arrangement equipped with the setting means for setting the manual timing, another drive means may be arranged. This drive means drives the second ultrasound transducer immediately after the drive means detects that the imaging ultrasound is reached to the second ultrasound transducer. In any of these arrangements, since the sound source image may appear on the ultrasound tomographic image and this sound source image is produced not only by the reflection wave response, but also the pulse-shaped ultrasound transmitted from the second ultrasound transducer itself, the position of the inserted second transducer can be clearly indicated even when the tomographic image is slightly disturbed by irradiating the focused ultrasound for therapeutical purposes. Eventually, it is possible to monitor as to whether or not the focused ultrasound for therapeutical purposes can be irradiated onto the correct position.

Also, an ultrasound therapy apparatus, according to another aspect of the present invention, is featured by such an ultrasound therapy apparatus comprising: a first ultrasound generating source for irradiating focused ultrasound used in therapeutical purposes; and an intraluminal catheter equipped with a second ultrasound generating source, which is used to be inserted into a region in the vicinity of an irradiation target region of the focused ultrasound; wherein: the ultrasound generated from the first ultrasound generating source is synthesized with ultrasound generated from the second ultrasound generating source so as to produce a standing wave. As a consequence, the generation of the cavitation can be easily controlled, and thus, the medical treatment can be carried out in a proper manner. It should also be noted that the frequency of the ultrasound generated from the second ultrasound generating source may be preferably "2n" times higher than, or "1/2n" times lower than the frequency of the ultrasound generated from the first ultrasound generating source, (symbol "n" is an integer more than, or equal to 1).

BEST MODE FOR CARRYING OUT THE INVENTION

Referring now to drawings, preferred embodiment modes of the present invention will be described.

Figure 1:
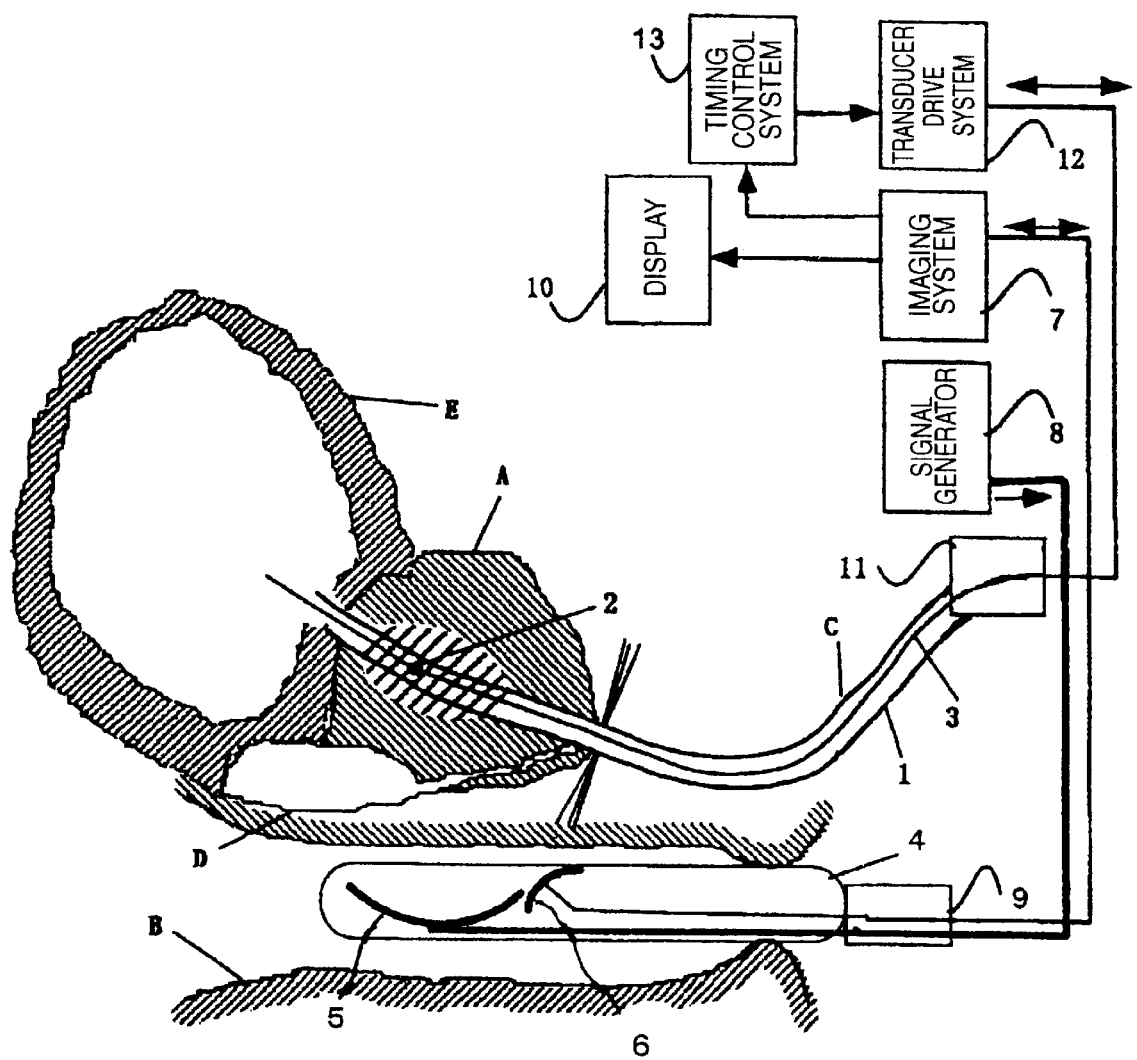
FIG. 1 is a structural diagram of an ultrasound therapy system for irradiating focused ultrasound according to an embodiment mode of the present invention.

FIG. 1 is a diagram for representing a structure of an ultrasound therapy apparatus (system) equipped with a medical catheter, according to a first embodiment mode of the present invention. This therapy apparatus is composed of an urethral catheter 1, an intrarectal ultrasound therapeutic applicator 4, an ultrasound imaging system 7, an electric signal generator 8 for therapeutic ultrasound, a position control system 9 of the ultrasound therapeutic applicator 4, a display 10, a transducer position control system 11 employed in the catheter 1, and a drive system 12 for driving a transducer employed in the catheter 1.

Figure 2:
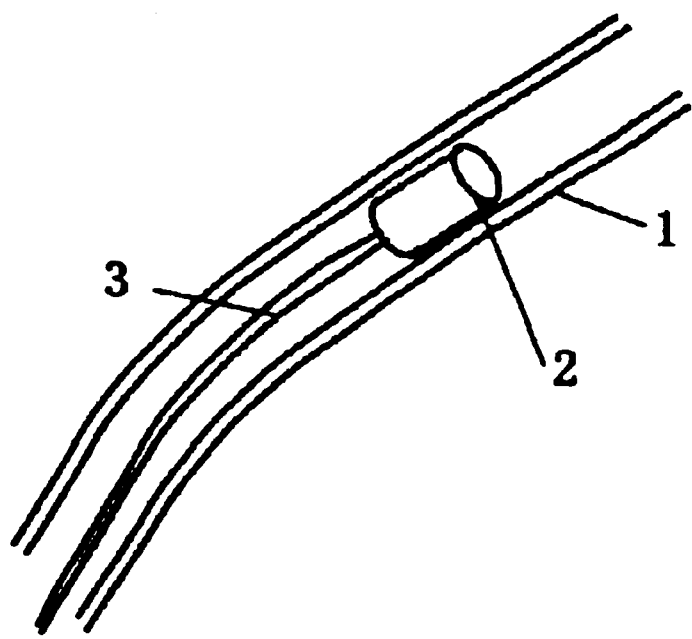
FIG. 2 is a constructive diagram of an intraluminal catheter according to the above-described embodiment mode.

FIG. 2 is a diagram for indicating a construction of an urethral catheter according to the first embodiment mode. An ultrasound transducer 2 constructed of a PZT piezoelectric element (resonant frequency is 4 MHz) having a diameter of 2 mm and a length of 5 mm is positioned inside a catheter outer wall 1 having an outer diameter of 5 mm and an inner diameter of 4 mm. A drive system of FIG. 2 is connected to the ultrasound transducer by employing a signal cable 3. Also, after the catheter 1 has been inserted into a urethra up to a predetermined depth, the position of the transducer 2 within the catheter 1 can be controlled by the transducer position control system 11.

Figure 3:
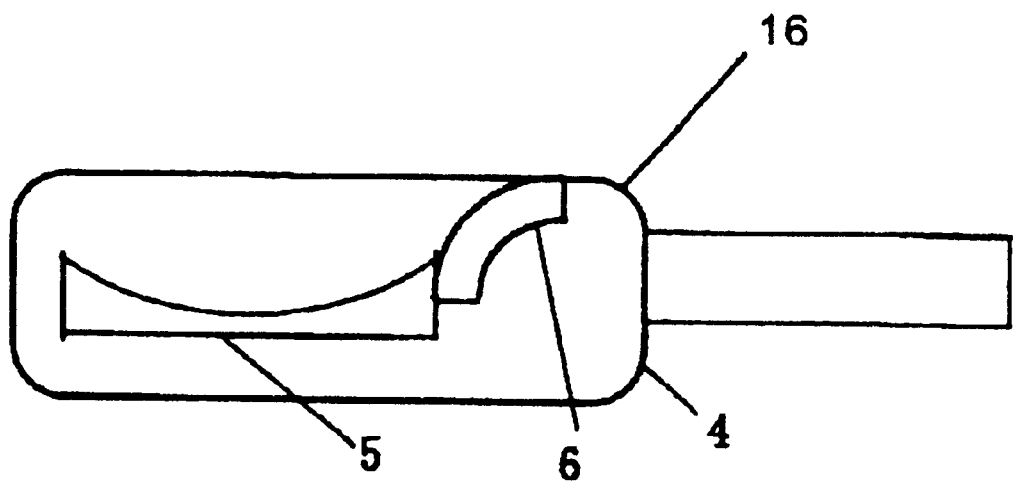
FIG. 3 is a constructive diagram of an ultrasound applicator of the above-explained embodiment mode.

FIG. 3 is a diagram for representing a construction of the ultrasound therapeutic irradiation applicator.4 according to the first embodiment mode. Both a focused ultrasound transducer 5 of a fixed focal point, which is constituted by a PZT piezoelectric element (F-value: 1 and resonant frequency: 3.3 MHz) having a diameter of 40 mm, and also an imaging ultrasound probe 6 are arranged within a cover 14 made of polyurethane, and are arranged in order that degased water may be filled thereinto.

The imaging ultrasound probe 6 corresponds to act convex type ultrasound probe which is arranged inside the applicator 4 in such a manner that a tomographic image of a section can be imaged and this section involves the focal point of the focused ultrasound transducer 5. A resonant frequency of an array transducer of this convex type ultrasound probe is identical to that of the transducer 2, namely 4 MHz. The imaging system of FIG. 1 may acquire an ultrasound tomographic image by the well-known convex scanning operation, while using the ultrasound probe. In other words, while the ultrasound transmitting aperture is sequentially shifted by selectively switching the transducer groups, the ultrasound transmitting operation of the imaging ultrasound pulse is repeatedly carried out. Also, in an ultrasound receiving term after each of the ultrasound transmitting operations, a similar selecting operation of the transducer group is performed. As a consequence, reflection wave responses are acquired by that the lateral direction is sequentially scanned. As is known in this technical field, it is desirable that focusing operations are made in proper depths while ultrasound is transmitted and also ultrasound is received, in view of the lateral resolution. The display 10 displays thereon the acquired ultrasound tomographic images. Also, a geometrical focal point of the focused ultrasound transducer is marked on this display screen of the display 10.

Subsequently, operations of this ultrasound therapy apparatus will now be explained in turn.

(1) Preparation

First, the catheter 1 is inserted into a urethra. Under this condition, the applicator 4 is inserted into a rectum. While the scanning operation of the imaging means 10 is carried out by employing the ultrasound diagnostic probe 6 positioned inside the applicator 4, an acquired ultrasound tomographic image of a body portion in the vicinity of a prostate is displayed on the display 10. Next, while the ultrasound tomographic image is observed, a positional relationship between a treatment region and the outer wall of the catheter 1 is recorded. In particular, when the tomographic image cannot be readily grasped, while such ultrasound having the same frequency as that of the diagnostic probe 6 is irradiated from the transducer 2, the transducer 2 is moved, so that the prostate may be auxiliarily searched based upon the position of the urethra.

(2) Target

While the ultrasound tomographic image acquired by the imaging ultrasound probe 6 is used, the position of the ultrasound therapeutic irradiating applicator 4 is adjusted in such a manner that the geometric focal point of the focused ultrasound transducer 5 employed in the applicator 4 is located on the treatment region. Next, the position of the transducer 2 provided within the catheter 1 is fixed in the vicinity of the prostate within the urethra, namely in the vicinity of the treatment region, and then the transducer 2 is driven by the drive system 12. The driving method realized by the drive system will be explained more in detail. Since the imaging operation of the imaging means is continuously carried out during also this drive operation, an image of a sound source is superimposed on the ultrasound tomographic image. This sound source image is caused by that the transducer 2 produces the ultrasound. At this time, a relative positional relationship between the geometric focal point of the focused ultrasound transducer 5 and this sound source image is recorded. Since the position of the first-mentioned geometric focal point of the transducer 5 is previously marked on the display screen, the latter-mentioned sound source image may be newly marked on this display screen. It should be noted that since an electric resettable marking means operated by a manipulation input is provided with the display 10, the above-explained marking operation of the sound source image may be easily carried out.

(3) Irradiation of Therapeutic Ultrasound

While the tomographic image acquired by the imaging means is displayed and the transducer 2 is driven, namely while the relative positional relationship is monitored on the displayed tomographic image, ultrasound for therapeutical purposes is irradiated from the focused ultrasonic transducer 5. The relative positional relationship is defined between the geometric focal point of the focused ultrasound transducer 5 and the sound source image indicative of the position of the transducer 2. As a typical irradiation condition, ultrasound intensity at the focal point is given by 2 KW·cm$^2$, and the ultrasound is irradiated for 4 seconds. When the above explained relative positional relationship is changed, namely in such a case that the appearing position of the actual sound source image is shifted with respect to the mark of the sound source image, the irradiation of the ultrasound is stopped.

Since the above-explained sound source image is produced not from the reflection wave, but from the ultrasound produced from the transducer 2, this sound source image may clearly appear on the tomographic image display screen even when the focused ultrasound for therapeutical purposes is irradiated, and thus it is possible to monitor such a fact that the focused ultrasound is irradiated onto the proper position. Alternatively, the ultrasound therapy apparatus may be arranged as follows. That is, when the ultrasound therapy apparatus detects that the appearing position of this sound source image is shifted from the mark position, the ultrasound irradiation may be automatically stopped.

(4) Scanning of Irradiation Region

While the tomographic image is observed, the sound source within the urethra is moved to a target region for irradiating treatment ultrasound, and a signal is sent to the applicator position control system 9 in such a manner that the shift between the sound source 2 within the urethra and the focal point of the therapeutic ultrasound is corrected on the image. Once the applicator is adjusted to a proper position, the irradiation of the therapeutic ultrasound is accomplished over an entire region of the target region for treatment by repeating targeting, irradiation, and the scanning operation.

Next, a description will now be made of the method for driving the transducer 2 according to this embodiment. There are two sorts of ultrasound signals generated from the transducer 2, namely a continuous wave and a pulse wave. When the continuous wave is employed, the sound source image of the transducer 2 becomes a line shape, and indicates only a lateral direction where the transducer 2 is present. A frequency of this continuous wave is identical to a frequency of pulse-shaped ultrasound transmitted from the imaging ultrasound probe 6.

Figure 4:
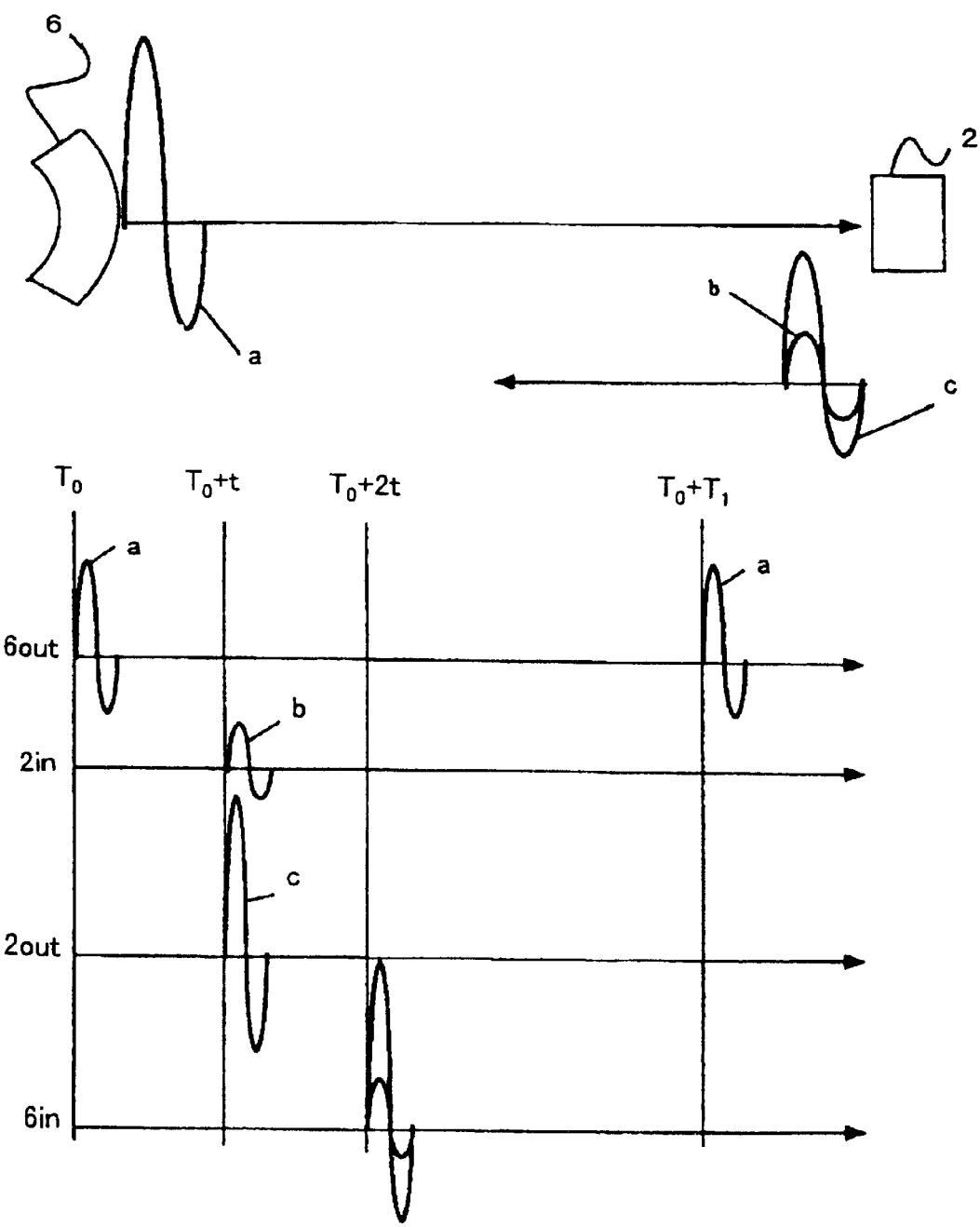
FIG. 4 is a waveform diagram for showing an example of a method for driving a transducer 2 of the above-explained embodiment mode.

On the other hand, when the pulse-shaped ultrasound is produced from the transducer 2, the resulting sound source image appeared on the display screen becomes a point shape. In order that this point-shaped sound source image correctly indicates a position of the transducer 2 on the display screen, namely both azimuth and a depth are correctly indicated, the transducer 2 must be driven in correct timing, while ultrasound transmission timing of the ultrasound probe 6 by the imaging means 7 is used as reference timing. Referring now to FIG. 4, this timing will be explained. Among ultrasound pulses which are sequentially transmitted from the ultrasound probe 6 by varying the azimuth, it is so assumed that an ultrasound pulse "a" transmitted along the direction of the transducer 2 is transmitted at a time instant "$T_0$", and then, this ultrasound pulse "a" is reached to the transducer 2 at a time instant "$T_0+t$." At this time instant "$T_0+t$", the transducer 2 is pulse-driven as indicated in "c." As a result, since the ultrasound pulse produced by driving the transducer 2 is also reached to the ultrasound probe 6 at a time instant "$T_0+2t$" when a reflection wave caused by the transducer 2 is reached to the ultrasonic probe 6, the sound source image by driving the transducer 2 may correctly indicate the position of the transducer 2. In order to realize such a correct drive timing, in this embodiment, a timing setting means 13 is provided. That is, while a trigger signal is used as a reference and this trigger signal represents a commencement of the scanning operation of the imaging means 7, this freely-adjustable timing setting means 13 sets producing timing of a drive waveform of the drive means 12 with respect to this trigger signal. The actual timing control is carried out by the ultrasound pulse driven by the drive means 12, while the ultrasound tomographic image displayed on the display 10 is observed. While both an image of the transducer 2 produced by a reflection response and another image produced by pulse-driving the transducer 2 will appear on the display screen, the timing control operation is accomplished when both the images are overlapped with each other. Such a timing control operation may be carried out every time the transducer 2 is moved, or the object under examination is moved due to body movement.

Alternatively, the above-explained arrangement may be replaced by the following arrangement. That is, while arrival time "t" of sound waves from the ultrasound probe 6 to the transducer 2 is previously measured, the drive system 12 may be operated in the pulse mode at such a timing delayed by this measurement "t" from the driving operation of the ultrasound probe 6.

Figure 5:
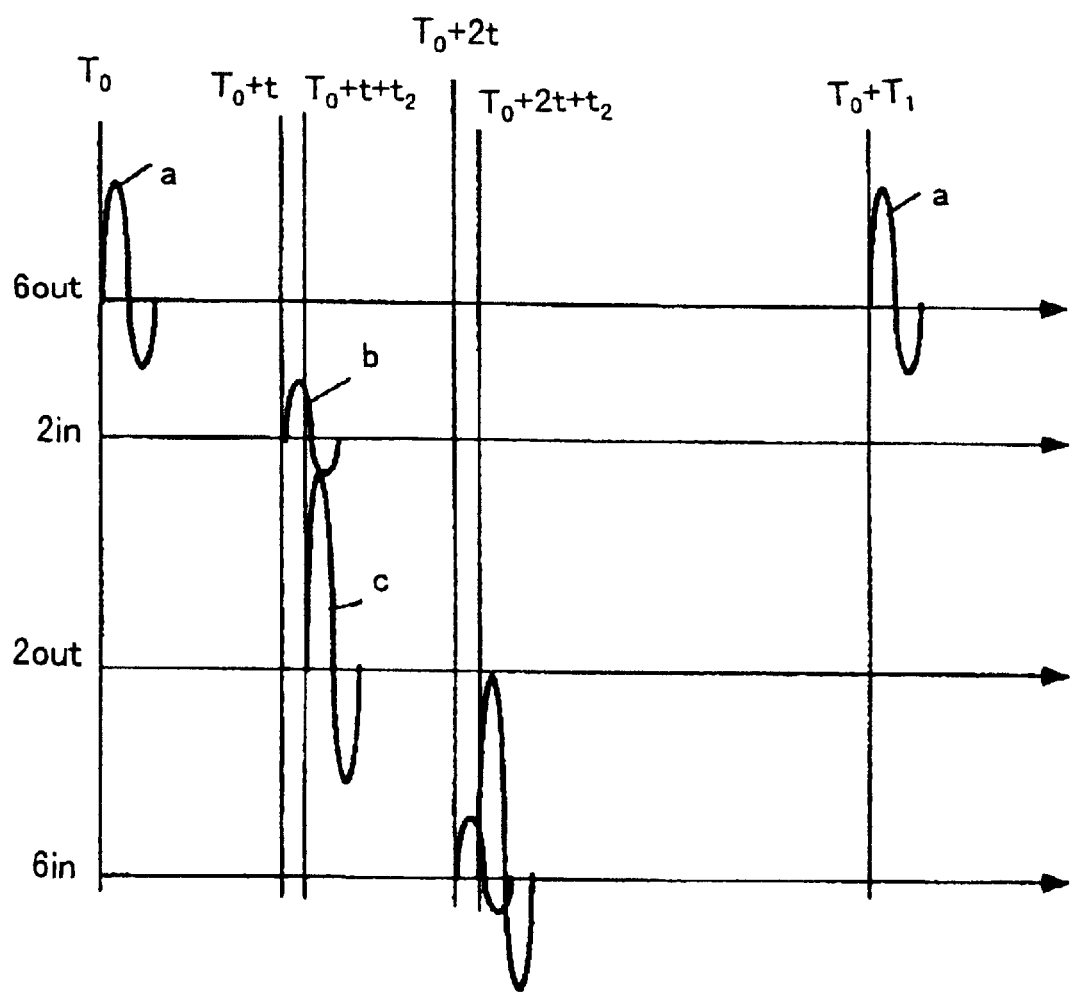
FIG. 5 is a waveform diagram for indicating another example of a method for driving the transducer 2 of the above-described embodiment mode.

A further arrangement of the drive system 12 may be employed, instead of the above-explained arrangement. That is, this arrangement may have such a function capable of detecting that imaging ultrasound produced from the ultrasound probe 6 toward the transducer 2 is reached to the transducer 2, and also have a function capable of immediately driving the transducer 2. Referring now to FIG. 5, when a pulse wave "b" transmitted from the ultrasonic probe 6 is received by the transducer 2, an electric signal "e" thereof is entered into the drive system 12, and this drive system 12 immediately drives the transducer 2 by a drive signal "f" while using this electric signal "e" as a trigger. In this alternative drive method, as shown in a lower portion of FIG. 5, an unavoidable small delay is practically produced for a pulse transmission "c" from the transducer 2 with respect to the ultrasound reception "b." However, this small delay does not cause any serious problem in this ultrasound therapy apparatus.

When the sound source provided in the urethra is employed, as explained above, there is the following merit, as compared with such a case that the catheter merely constitutes the reflection article. That is, both the amplitude direction and the radiation direction can be controlled.

Figure 6:
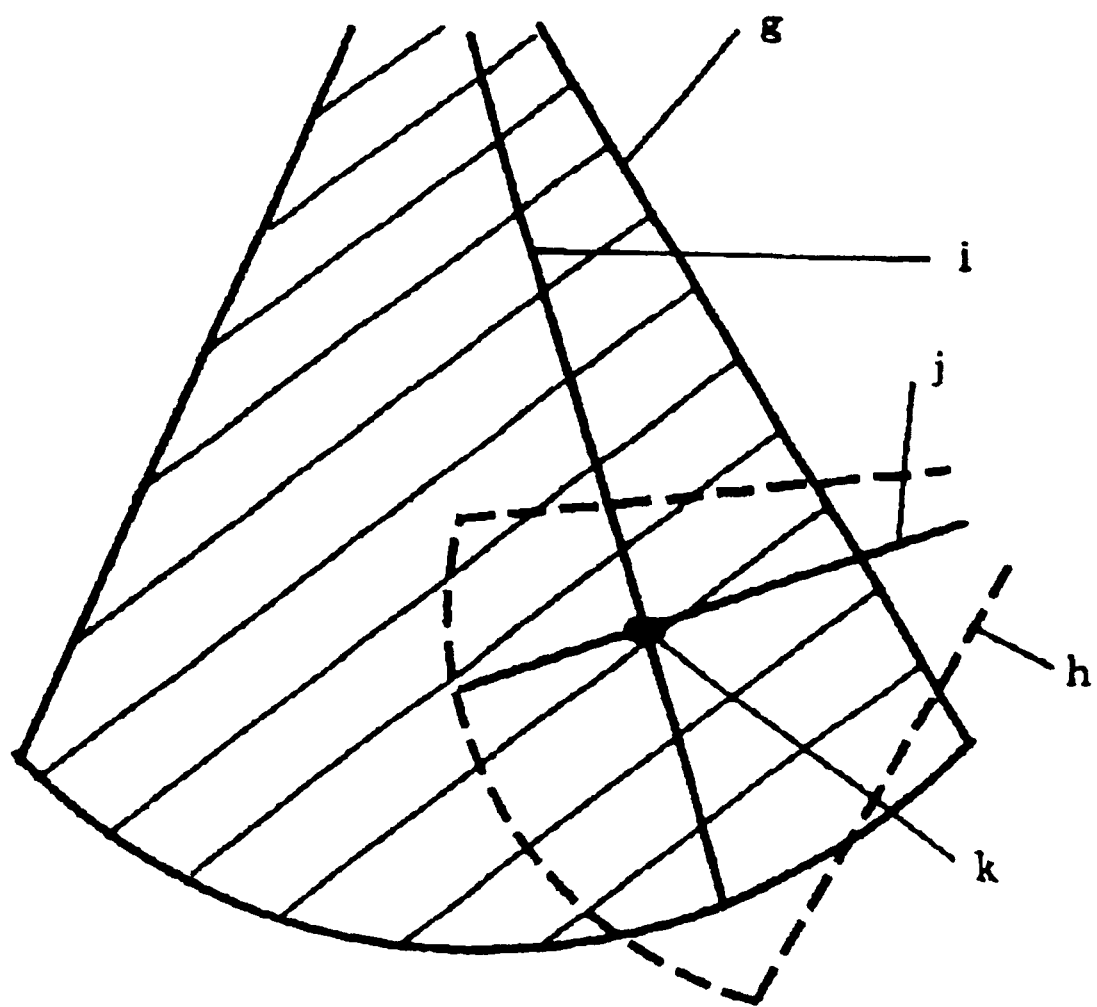
FIG. 6 is a diagram for representing a tomographic image produced in such a case that the transducer 2 of the above-described embodiment mode is driven by a further driving method.
Figure 8:
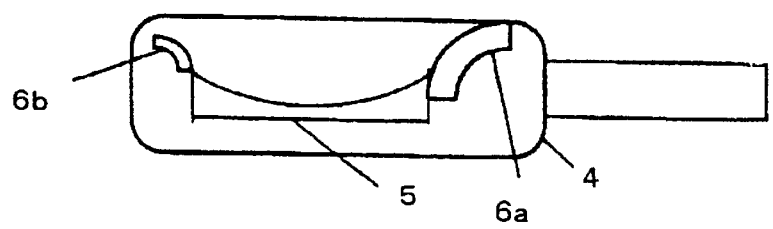
FIG. 8 is a constructive diagram of an intraluminal applicator equipped with an auxiliary probe according to a further embodiment mode of the present invention.

As described above, the method for using the continuous wave may also own a merit in addition to the method for employing the pulse wave, in view of the S/N ratio. In the case that the continuous wave is employed, the ultrasound signal generated from the ultrasound generating source 2 is modified, and then, the modified ultrasound signal is detected by way of the Lock-In detection manner on the diagnostic screen, so that even on the diagnostic screen having the low S/N adversely deteriorated by the therapeutic ultrasound, the direction of the ultrasound generating source 2 can be sufficiently observed. When the continuous wave is employed, since the information as to the depth direction is lost, it is desirable to employ an auxiliary probe 6b as indicated in FIG. 8 as a method capable of compensating for the information of the depth direction. This is realized by providing an auxiliary probe with the intraluminal applicator of FIG. 3. Since these two ultrasound probes are employed, even when only the information related to the respective directions is acquired, the position of the ultrasound generating source 2 may be obtained as a cross point of a line which is extended from this ultrasound sound source 2 along the ultrasound arriving direction on the diagnostic screen. Referring now to FIG. 6, it is so assumed that a b-mode image produced by an ultrasound probe 6a is "g", and another b-mode image produced by another ultrasound probe 6b is "h." At this time, since a signal produced by the ultrasound sound source 2 becomes a line "i" produced by the ultrasound probe 6a and another line "j" produced by the ultrasound probe 6b on the screen, a cross point "k" may be understood as the position of the transducer 2. At this time, since the auxiliary probe is not equal to such a probe used to acquire a diagnostic image, such a probe whose total element number is small is preferably employed so as to reduce the volume of the intraluminal applicator.

Also, the therapeutic effects may be improved by generating the ultrasound from the transducer 2. For example, when the focused ultrasound is generated from the transducer 6, at the same time, ultrasound having the same frequency as that of the focused ultrasound is generated. Alternatively, such ultrasound having a frequency "2n" times higher than, or "1/2n" times lower than the frequency of the focused ultrasound is generated (symbol "n" is integer more than, or equal to 1). While a generation of cavitation can be easily controlled by selecting intensity of generated ultrasound and also a frequency of this generated ultrasound, the therapeutic effects may be achieved by utilizing either the chemical operation or the chance operation of the cavitation. Alternatively, when such a transducer having one-dimensional array-shaped plural elements is employed instead of the above-described transducer 2, such an acoustic field suitable for the cavitation may be freely formed by directly returning ultrasound having the same frequency along the incident direction of the focused ultrasound.

Next, a second embodiment mode of the present invention will now be explained with reference to FIG. 7. In this embodiment mode, since the transducer 2 is used as an acoustic intensity sensor, a focal point of focused ultrasound may be focused onto a target region, and a change in relative positions between the focal point and the target region may be monitored.

Figure 7:
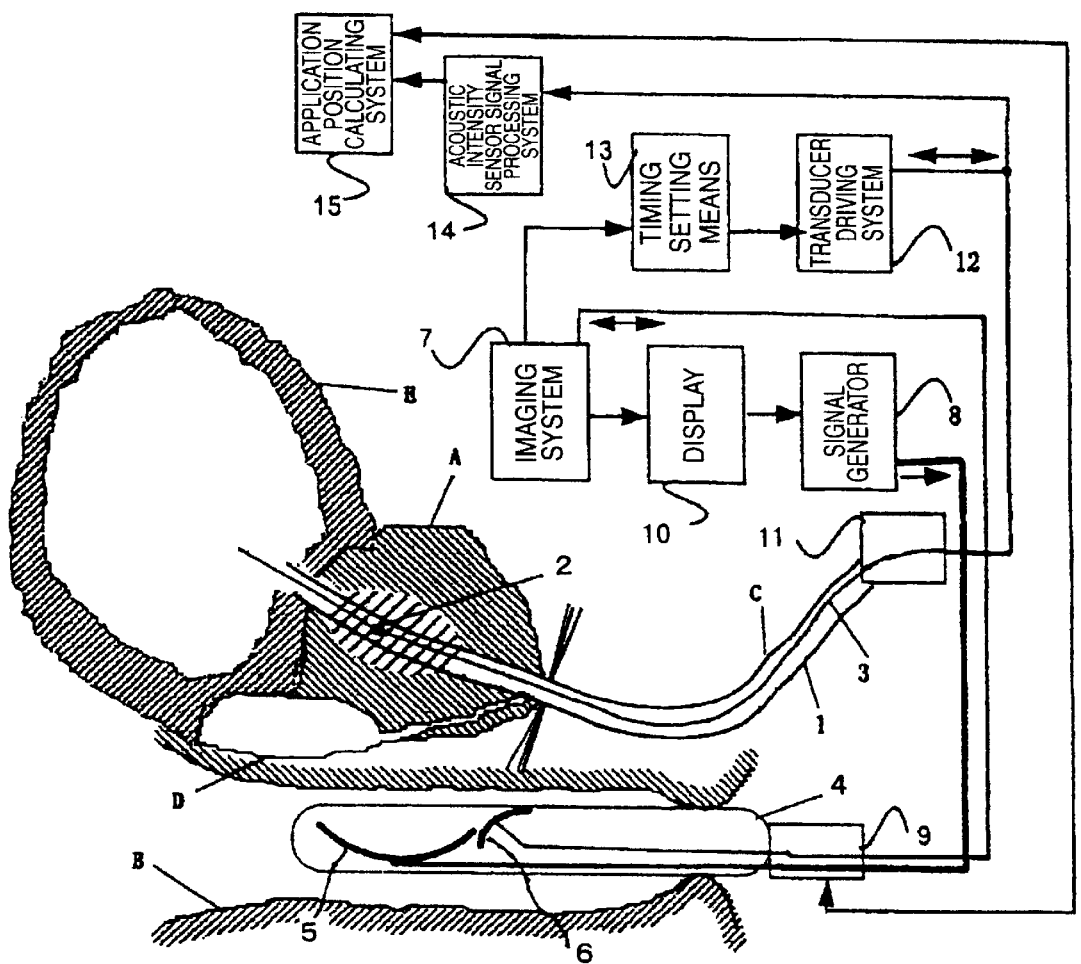
FIG. 7 is a structural diagram of an ultrasound therapy system according to another embodiment mode of the present invention.

FIG. 7 is a structural diagram of an ultrasound therapy apparatus (system) of this second embodiment mode, which is realized by adding an acoustic intensity sensor signal processing system 14 to the construction of FIG. 1. It should be noted that the same reference numerals shown in FIG. 1 indicate the same components in this drawing. A procedure of a treatment is given as follows:

(1) Targeting

Positioning of the ultrasound transducer 2 is carried out in a similar manner to that of the first embodiment mode. Next, focused ultrasound is preliminarily irradiated from the focused transducer 5 at intensity $1/10$ times lower than such intensity of ultrasound which will be later irradiated for therapeutical purposes. At this time, a signal which is acquired by the ultrasound transducer 2, namely, an acoustic intensity sensor signal is acquired by the acoustic intensity sensor signal processing system 14. An output signal of this acoustic intensity sensor signal processing unit 14 is equal to sound-pressure intensity at the position of the transducer 2, and is entered into an applicator position calculating system 15. The above-explained focused ultrasound is repeatedly carried out in an interrupt manner. While this irradiation of the focused ultrasound is repeated, the applicator position calculating unit 15 sequentially outputs to an applicator control system 9, such a signal capable of very slightly changing an insertion depth and a position of the applicator 4. Every time this signal is outputted to the applicator control unit 9, the applicator position calculating unit 15 records sound-pressure intensity so as to search an insertion depth and an attitude of the applicator 4 under which maximum sound-pressure intensity can be obtained. This searching operation may be realized by the hill-climbing method known in this technical field. When the searching operation is ended, the applicator 4 is fixed at the depth and the attitude, under which the sound-pressure intensity becomes maximum.

(2) Irradiation

When the relative position is determined by the above-explained targeting operation, the focused ultrasound for therapeutical purposes is subsequently irradiated from the focused transducer 5. Also, while the focused ultrasound is irradiated, the sound-pressure intensity is monitored by utilizing the acoustic intensity sensor signal acquired from the transducer 2. Thus, it is possible to confirm that the focal position is not shifted.

While the position of the transducer 2 provided in the catheter is sequentially moved in the first stage, since both the above-explained operations defined in the items (1) and (2) are successively carried out, the entire region located along the urethra of the prostate can be easily treated.

In the above-described embodiment mode, the ultrasound therapy apparatus is arranged by that both the insertion depth and the attitude of the applicator 4 are very slightly changed by the applicator position calculating system 15 and the position control system 9 until the sound-pressure intensity becomes maximum. Alternatively, this therapy apparatus may be arranged by that all of the position and the attitude of the applicator 4 may be manually manipulated.

Next, an ultrasound therapy apparatus according to a third embodiment mode of the present invention will now be explained. In the above-explained second embodiment mode, the acoustic intensity sensor is employed so as to monitor the irradiation position. In contrast, in the third embodiment mode, a temperature sensor is employed in order to directly observe effects of focused ultrasound for therapeutical purposes. An arrangement of this ultrasound therapy apparatus is realized by additionally employing a temperature sensor in the ultrasound transducer 2 provided in the catheter of FIG. 7, and furthermore by providing a temperature sensor signal processing unit instead of the acoustic intensity sensor signal processing system 14.

Prior to irradiation of focused ultrasound, the targeting is carried out by adjusting an insertion depth and an attitude of the applicator 4, while monitoring an image appearing position of the transducer 2 on an ultrasound tomographic image similar to the first embodiment mode. The focused ultrasound for therapeutical purposes is irradiated while temperatures are observed. When the temperatures are increased in correspondence with the irradiation of the ultrasound, it is predictable that the focused ultrasound can be correctly directed to a treatment region. At this time, the irradiation time and the irradiation intensity of the focused ultrasound can be controlled in such a manner that the temperature at the treatment region becomes higher than, or equal to a coagulation point of protein, and also becomes lower than, or equal to a boiling point of water, typically is approximated to 80° C.

The present invention is not limited to the above-specified embodiment modes, but may be modified without departing from the technical spirit and scope of the present invention.

Industrial Applicability

In accordance with the present invention, even while the focused ultrasound is irradiated, it is possible to monitor as to whether or not this focused ultrasound is correctly directed to the treatment region. As a consequence, it is possible to avoid such an erroneous irradiation that the focused ultrasound is irradiated onto any region other than the target region, which is caused by the positional shift. Also, the safety treatment can be carried out as to the target region which is located close to such a region to which the focused ultrasound is not wanted to be irradiated. Also, since the targeting ultrasound is overlapped, or superimposed on the focused ultrasound for therapeutical purposes, the cavitation effect can be increased and also the therapeutical effects can be improved.

What is claimed is:

1. An ultrasound therapy apparatus comprising:
   a first ultrasound transducer for generating focused ultrasound used in therapeutical purposes;
   an ultrasound probe arranged in such a manner that said ultrasound probe is moved in combination with said first ultrasound transducer;
   an intraluminal catheter used to be inserted into a region in the vicinity of an irradiation target region of said focused ultrasound; and
   imaging means for forming an ultrasound tomographic image in such a manner that while imaging ultrasound is repeatedly transmitted from said ultrasound probe, reflection wave responses are acquired by sequentially scanning reception signals of reflection signals thereof along a lateral direction; wherein:
   said intraluminal catheter is comprised of:
      a second ultrasound transducer; and
      drive means for driving said second ultrasound transducer to generate ultrasound during an imaging operation by said ultrasound imaging means; and also
   said imaging means superimposes a sound source image which is caused by the ultrasound produced by said second ultrasound transducer on said ultrasound tomographic image.

2. An ultrasound therapy apparatus as claimed in claim 1 wherein:
   said drive means drives said second ultrasound transducer in a pulse-shape mode, so that said imaging means superimposes a point-shaped sound source image which is caused by pulse-shaped ultrasound generated from said second ultrasound transducer on said ultrasound tomographic image.

3. An ultrasound therapy apparatus as claimed in claim 2 wherein:
   said drive means is comprised of:
      setting means for setting that drive timing of said second ultrasound transducer is adjustable with respect to the repetitive ultrasound transmission by said imaging means.

4. An ultrasound therapy apparatus as claimed in claim 2 wherein:
   said drive means drives said second ultrasound transducer immediately after said drive means detects that said imaging ultrasound is reached to said second ultrasound transducer.

5. An ultrasound therapy apparatus as claimed in claim 2 wherein:
   said ultrasound therapy apparatus is further comprised of:
      marking means for electrically marking a position of said point-shaped sound source image which is superimposed on said ultrasound tomographic image; and said ultrasound imaging means displays said point-shaped sound source image on the position of said second ultrasound transducer, which can be compared with the position of the point-shaped sound source image marked by said marking means, while the focused ultrasound for therapeutical purposes is irradiated.

6. An ultrasound therapy apparatus as claimed in claim 5 wherein:

said ultrasound therapy apparatus is further comprised of:
means for stopping the irradiation of said focused ultrasound for therapeutical purposes when an appearing position of said point-shaped sound source image is shifted from the position marked by said marking means, while the focused ultrasound for therapeutical purposes is irradiated.

7. An ultrasound therapy apparatus comprising:

a first ultrasound generating source for irradiating focused ultrasound used in therapeutical purposes to a patient;

an ultrasound probe arranged in such a manner that said ultrasound probe is moved in combination with said first ultrasound generating source;

ultrasound imaging means for imaging an ultrasound tomographic image used in a positioning operation with employment of said ultrasound probe; and an intraluminal catheter equipped with a second ultrasound generating source, which is used to be inserted into a region in the vicinity of an irradiation target region of said focused ultrasound; wherein:
under such a mutual positional condition that said second ultrasound generating source is fixed in the vicinity of said irradiation target region and also a geometrical focal point of said first ultrasound generating source is made coincident with said irradiation target portion, said second ultrasound generating source is driven at the same time when said first ultrasound generating source is driven at the same frequencies, or at a frequency "2n" times higher than, or "1/2n" times lower than, or equal to the frequency of said first ultrasound generating source, whereby said second ultrasound generating source generates ultrasound which is returned from said first ultrasound generating source to a direction along which said focused ultrasound for therapeutical purposes is entered.

8. An ultrasound therapy apparatus comprising:

a first ultrasound transducer for generating focused ultrasound used in therapeutical purposes;

an ultrasound probe arranged in such a manner that said ultrasound probe is moved in combination with said first ultrasound transducer;

an intraluminal catheter used to be inserted into a region in the vicinity of an irradiation target region of said focused ultrasound; and imaging means for forming an ultrasound tomographic image in such a manner that while imaging ultrasound is repeatedly transmitted from said ultrasound probe, reflection wave responses are acquired by sequentially scanning reception signals of reflection signals thereof along a lateral direction; wherein:
said intraluminal catheter is comprised of:
a second ultrasound transducer for detecting acoustic intensity which is caused by said focused ultrasound.

9. An ultrasound therapy apparatus as claimed in claim 1 wherein:

while said first ultrasound transducer is positioned, said drive means drives said second ultrasound transducer at the same frequency as that of said imaging ultrasound; and during a medical treatment term after a positioning of said first ultrasound transducer, said drive means drives said second ultrasound transducer at the same time when the focused ultrasound for therapeutical purposes is irradiated from said first ultrasound transducer at the same frequency as that of said therapeutical ultrasound, or at a frequency "2n higher than, or "1/2n" times lower than, or equal to said frequency of the therapeutical ultrasound, symbol "n" being an integer more than, or equal to 1.

* * * * *